United States Patent [19]

Matsumura

[11] Patent Number: 5,328,614
[45] Date of Patent: Jul. 12, 1994

[54] METHODS AND APPARATI FOR REMOVING PROTEIN-BOUND MOLECULES FROM BODY FLUIDS

[76] Inventor: Kenneth N. Matsumura, 2107 Dwight Way, Berkeley, Calif. 94704

[21] Appl. No.: 816,652

[22] Filed: Jan. 3, 1992

Related U.S. Application Data

[63] Continuation-in-part of Ser. No. 274,028, Nov. 21, 1988, Pat. No. 5,078,885, which is a continuation-in-part of Ser. No. 499,877, Jun. 1, 1983, abandoned, which is a continuation-in-part of Ser. No. 209,282, Nov. 18, 1980, abandoned, which is a continuation-in-part of Ser. No. 40,892, May 21, 1979, abandoned.

[51] Int. Cl.$^5$ ............................................. B01D 61/24
[52] U.S. Cl. .................................... 210/632; 210/638; 210/321.75
[58] Field of Search .................... 210/632, 638, 34.72, 210/34.75

[56] References Cited

U.S. PATENT DOCUMENTS

| | | | |
|---|---|---|---|
| 2,982,416 | 5/1961 | Bell | 210/321.75 |
| 3,734,851 | 5/1973 | Matsumura | 210/321.75 X |
| 5,078,885 | 1/1992 | Matsumura | 210/321.72 X |

Primary Examiner—Frank Spear

[57] ABSTRACT

Apparatus and method wherein body fluid to be treated flows proximate the surface of hepatocytes, the hepatocyte treatment of said body fluid substantially being made to occur across a layer of albumin concentration substantially greater than the concentration in said body fluid, the albumin layer being less than 3 microns.

7 Claims, 12 Drawing Sheets

TO INTERIOR OF MEMBRANE

A = ALBUMIN
* = BILIRUBIN
DA = DESIGNER ADSORBENT

TO INTERIOR OF MEMBRANE

LAYER OF INCREASED
ALBUMIN CONCENTRATION

METHODS AND APPARATI FOR REMOVING PROTEIN-BOUND MOLECULES FROM BODY FLUIDS

FIELD OF THE INVENTION

This application is a continuation-in-part of U.S. application Ser. No. 274,028 filed Nov. 21, 1988 now U.S. Pat. No. 5,078,885, which is a continuation-in-part of Ser. No. 499,877 filed Jun. 1, 1983 now abandoned, which is a continuation-in-part of Ser. No. 209,282 filed Nov. 18, 1980 now abandoned, which is a continuation-in-part of Ser. No. 040,892 filed May 21, 1979 now abandoned.

This invention is in the field of treatment of body fluids and more specifically deals with an improved method for the removal of protein-bound molecules from body fluids.

BACKGROUND OF THE INVENTION

Standard hemodialysis readily removes molecules (e.g., urea, raffinose, and potassium) in the body fluids which are free and not bound to other molecules like proteins. However, molecules such as jaundice-causing bilirubin and tranquilizer diazepam can not be removed from body fluids by standard hemodialysis because such molecules, though small, are bound to larger molecules like albumin (MW 69,000) and other proteins present in the body fluids: standard hemodialysis membranes are not permeable to albumin or large proteins because their pores are too tiny to admit them (FIG. 1); consequently molecules bound to large proteins remain stuck to the proteins and do not cross the membrane.

Some years ago, I invented a hybrid bio-artificial liver (U.S. patent Ser. No. 3,734,851) which works on the principle of flowing body fluid across one side of a semi-permeable membrane while keeping living liver cells (hepatocytes) proximate opposite side of said membrane. The membrane was physiologically semi-permeable in that the porosity allowed cross-over of molecules such as nutrients, toxins, proteins, and hepatocyte-secretory products, but prevented the cross-over of cells such as lymphocytes in the body fluid which can immunologically reject and kill the hepatocytes. Protein-bound toxins that are normally removed by the liver are also removed by my bio-artificial liver.

However, it became advantageous to use animal hepatocytes to treat human beings because animal hepatocytes are more readily available in quantity and are generally cheaper than human hepatocytes. Because it can be disadvantageous to allow contamination of human body fluid with animal proteins, it was felt best to use a semi-permeable membrane that would not allow the cross-over of proteins like albumin. It was discovered, however, that just any randomly selected membrane impervious to proteins would not work well in my bio-artificial liver because protein-bound toxins and substances in the body fluid remained unremoved. Work was done to figure out how to remove protein-bound substances while still using semi-permeable membrane that would not allow the cross-over of proteins.

While conducting extensive studies over many years on the removal of protein-bound substances by hepatocytes, some other interesting observations were made which became the bases of the invention described herein.

If one flows body fluid containing bilirubin molecules that are bound to albumin simply across the surface of hepatocytes extracted from liver tissue, one is surprised to find that the hepatocytes do not remove the bilirubin molecules as well as would be commonly expected. Those skilled in the art had always believed that one can create a bio-hybrid artificial liver by simply passing body fluid across the surfaces of hepatocytes which are isolated from liver and which are attached to a solid surface such as a membrane or beads. As the inventor of the first practical bio-artificial liver (cited above), I also believed the same, that the only ingredients needed for a fully functional bio-artificial liver were 1) live hepatocytes and 2) flowing body fluid that can feed nutrients and oxygen to the liver cells. While my bio-artificial liver of the aforementioned patent employed a semi-permeable membrane interposed between the flowing body fluid and the hepatocytes proximate the membrane, I had intended that the purpose of the membrane was purely to prevent the flowing body fluid from washing away the hepatocytes and to prevent immunologic cells in the body fluid from attacking and destroying the hepatocytes which may be invariably immunologically incompatible with the patient from which the body fluid flowed. For this reason, this semi-permeable membrane was exactly that: semi-permeable. I specified that the membrane be permeable to molecules but that it allows no immunologic cells to cross the pores of the membrane even over time slowly.

As other technologies developed so that 1) hepatocytes can be attached so securely to a solid surface so as to make their washing away no longer a problem, and 2) immunologic rejection of hepatocytes can be prevented without a semi-permeable membrane, I began to envision a bio-artificial liver using no semi-permeable membrane where hepatocytes would be bathed directly in the flowing body fluid. As we began to have success in growing human hepatocytes in culture, it became possible to consider a bio-artificial liver using no semi-permeable membrane which would be no longer necessary to block contamination of the treated body fluid with animal proteins from animal hepatocytes. It was expected that such a bio-artificial liver would be more efficient since molecules to be treated in the body fluid did not have the obstacle of having to cross the membrane to be taken up by the hepatocytes. In fact, others (B. Eiseman, L. Norton, N. C. Kralios, Surg. Gyn. Obst. 142:21–28, Jan. 1976; J. Uchino, et al. Proc. Am. Soc. Artif. Intern. Organs 34:972–977, 1988; K. Yanagi, et al. Proc. Am. Soc. Artif. Intern. Organs 36:M727–M729, 1990; T. Soyer et al. Annals of Surg. 177:393–401, 1973) proposed bio-artificial livers in which hepatocytes were directly bathed by flowing body fluids such as plasma from a continuous plasmapheresis device. Although it has not been publicly reported, nothing has yet come of bio-artificial livers not using an interposing semi-permeable membrane between hepatocytes and body fluid.

In light of the the discoveries I have been making over the past twenty years pertaining to the removal of protein-bound substances from plasma by hepatocytes, it is now not surprising that a bio-artificial liver does not efficiently remove protein-bound bilirubin if one simply flows body fluid across the surfaces of hepatocytes.

What I have learned mostly through experimentation is that it is necessary to interpose a layer of substantially increased albumin concentration between the flowing body fluid and the hepatocytes.

SUMMARY OF THE INVENTION

I have developed novel methods for removing from body fluids molecules which are protein-bound. The methods are a great boon to the practice of the bio-artificial liver/body fluid purifier that I developed (U.S. Pat. No. 3,734,851, cited above) and to the modifications thereof, and for the removal of toxic levels of many drugs from body fluids. Other objects and benefits of my invention will become evident in the course of the description which follows.

Generally, in the method comprising positioning body fluid to be treated into contact with one side of a semi-permeable membrane and positioning adsorbent proximate the other side of said membrane, one part of my new invention is the improvement for removing molecules which are bound to proteins in body fluid comprising positioning said body fluid in contact with one side of an albumin-dimensioned bottle-neck pore membrane and positioning proximate the opposite side of said membrane aqueously suspended adsorbent. A further improvement comprises providing means for minute, rapid, to-and-fro partial movement of adsorbents and body fluid proteins into and out of narrow end of the pores of said membrane. In another preferred embodiment, said adsorbents, including hepatocytes, are placed most proximate to the permeability governing active layer side of asymmetric membrane having permeability cut-off under the molecular weight of albumin.

In the apparatus comprising a semi-permeable membrane, means associated therewith for positioning body fluid to be treated in contact with one side of said membrane and adsorbents located proximate the opposite side of said membrane, the apparatus of my invention is the improvement comprising an albumin-dimensioned bottle-neck pore membrane and means associated therewith for positioning body fluid to be treated in contact with one side of said membrane and aqueously suspended adsorbent located proximate the opposite side of said membrane. In another embodiment, the apparatus of my invention is the improvement comprising an asymmetric membrane with permeability cut-off under the molecular weight of albumin and means associated therewith for positioning body fluid to be treated in contact with the more porous side of said membrane and aqueously suspended adsorbent located proximate the permeability governing active layer side of said membrane.

While animal hepatocytes suffice in most cases for treating hepatic failure in humans, there are instances in which it would be advantageous to have human hepatocytes in an artificial liver system. Because in general animal hepatocytes are less expensive and more available, it would be advantageous to make use of animal hepatocytes in addition to human hepatocytes. Sometimes, it is possible to circumvent the lesser immunologic incompatibility between human beings but not possible to circumvent the greater immunologic incompatibility between human and animals. Then one can dispense with the semi-permeable membrane in the part of the system using human hepatocytes, but one would need to retain the semi-permeable membrane in that part of the system using animal hepatocytes to prevent immunologic rejection.

Therefore, in another part of my invention, body fluid to be treated flows proximate the surface of hepatocytes, said hepatocyte treatment of said body fluid substantially being made to occur across a layer of albumin concentration substantially greater than the concentration in said body fluid, said albumin layer being less than 3 microns.

DETAILED DESCRIPTION OF THE INVENTION

Figure 1:
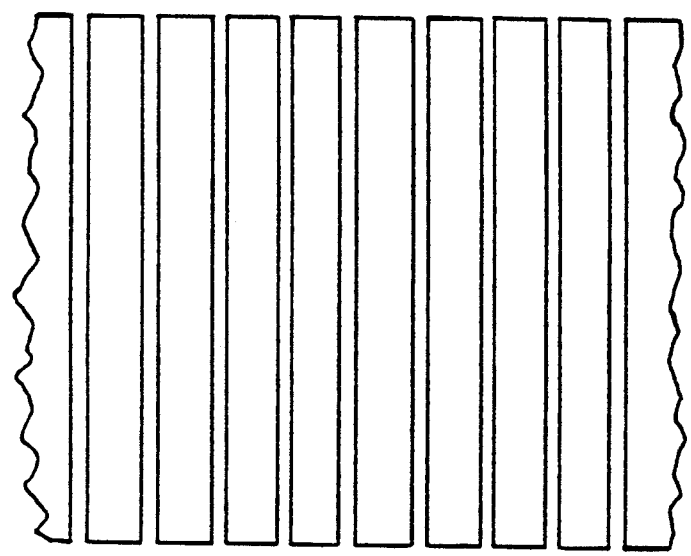
FIG. 1 is a cross-section of a standard hemodialysis membrane. Note the uniform diameter of the pore throughout its length. It is not possible to remove protein bound molecules from body fluids using this type of membrane.
Figure 2A:
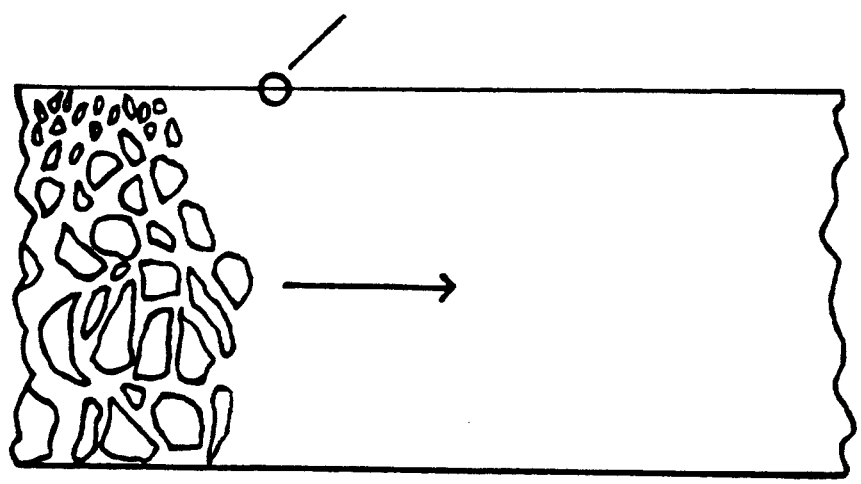
FIG. 2a is a cross-section of the novel bottle-neck pore membrane which, together with adsorbents, allows the removal of molecules which are bound to proteins in the body fluid. The removal is accomplished without the loss of vital body fluid proteins like albumin.
Figure 2B:
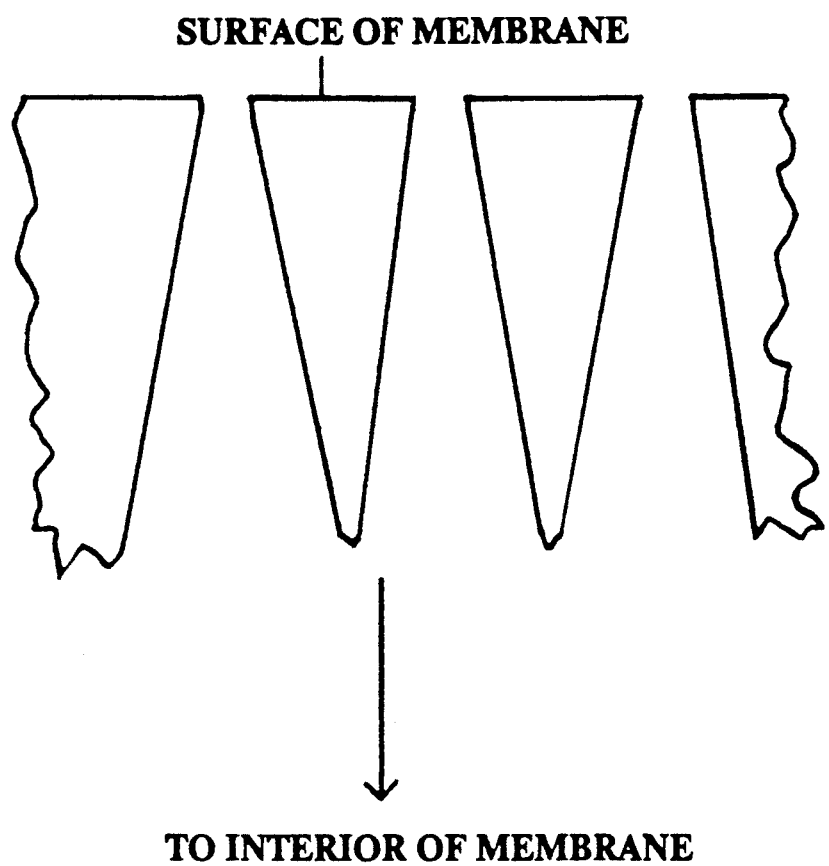
FIG. 2b is a blown up image of the cross-section at center of the circle in FIG. 2a. The pore size becomes smaller and smaller towards the surface on this side of the membrane. However the requirment at the bottle-neck end of the pores is a functional one. The vertical dimension at the bottle neck is the minimum necessary relative to the pore size to block the complete cross over of the albumin molecule to the other side of the membrane. Beyond the bottle-neck, the pore widens immediately as it courses into the interior of the membrane.
Figure 3:
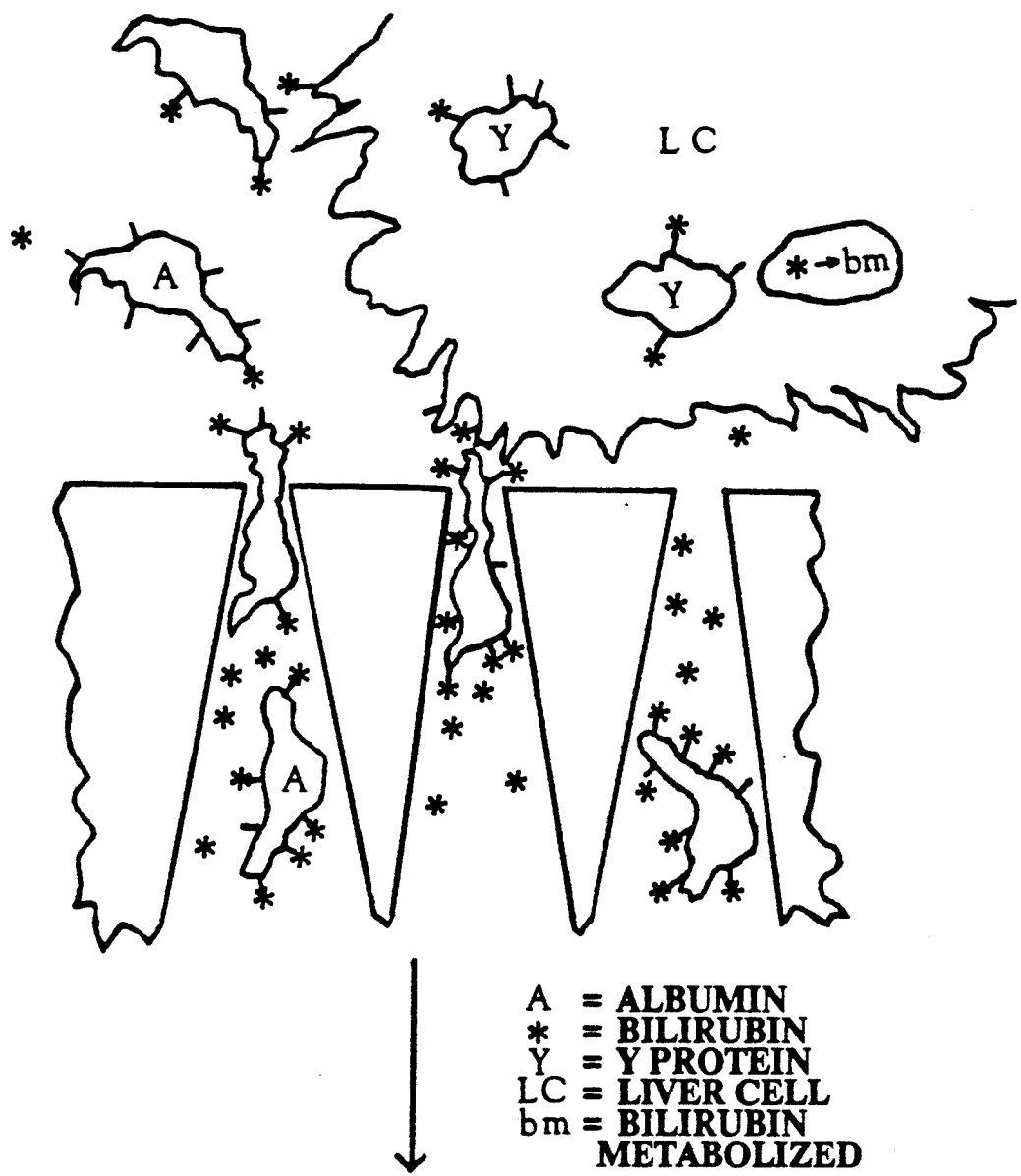
FIG. 3 shows that the narrow bottle-neck end of the pores prevents body fluid proteins like albumin from completely crossing the membrane; in a preferred embodiment, however, the bottle-neck is so dimensioned that a substantial portion of the protein molecule can cross the narrow end and extend itself out of the bottle-neck area to the other side of the membrane. While "waving" its arm on the other side of the membrane, the body fluid proteins can contact adsorbents on the other side. During this contact, adsorbents can "grab" away molecules like bilirubin which are loosely bound to the body fluid proteins. When this type of direct contact is possible between the adsorbent and the albumin, transfer kinetics of the bound molecules are maximal. However, short of achieving direct contacts, bringing the albumin molecule and the adsorbent as close as possible considerably enhances the transfer of the bound molecules across the membrane.
Figure 4:
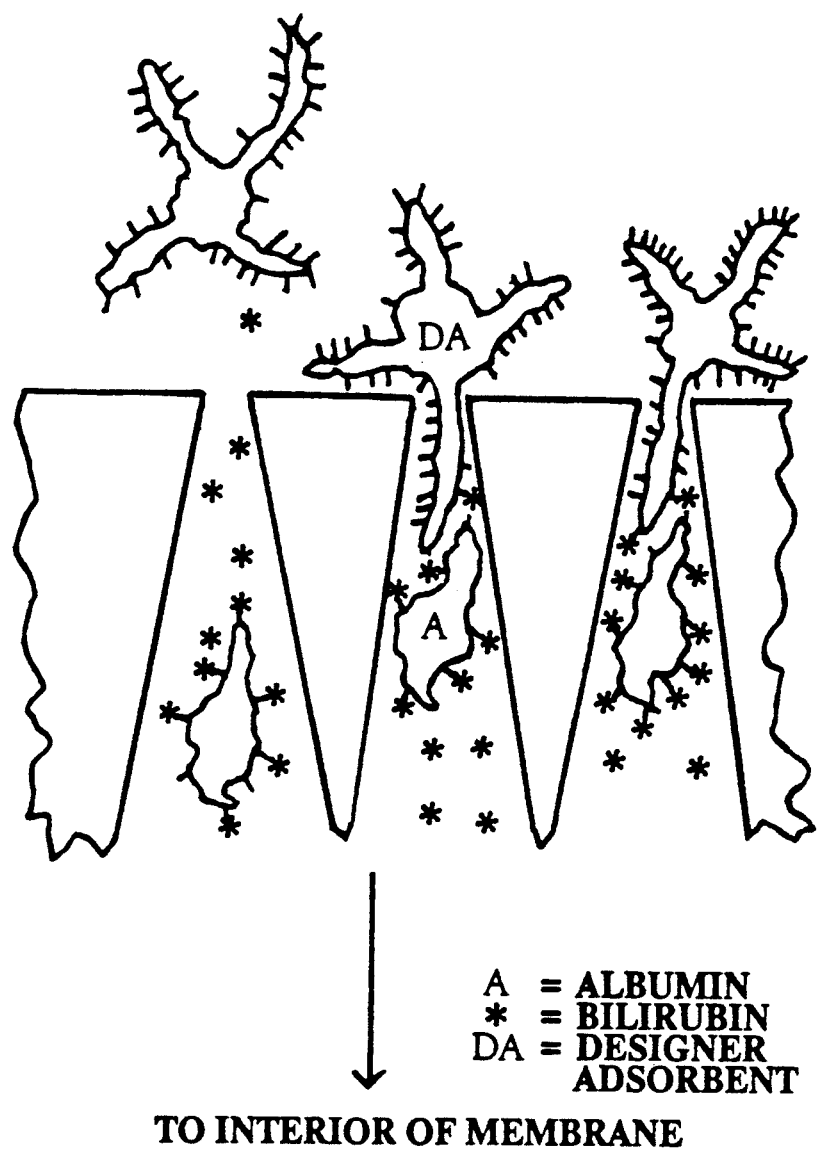
FIG. 4 shows that the narrow bottle-neck end of the pores prevents adsorbents from completely crossing the narrow end of the pores. However, in a preferred embodiment, the bottle-neck and the adsorbent are so dimensioned that a substantial portion (i.e., the binding arm) of the adsorbent can cross the bottle-neck end into the depth of the pores. In the depth of the pores, the adsorbents contact body fluid proteins from the other side of the membrane and "grab" away molecules such as bilirubin which are loosely bound to body fluid proteins.

By albumin-dimensioned bottle-neck pore membrane, I mean a membrane like that shown in FIG. 2a and 2b. It can be of various materials, including cellulose acetate. Given the specification contained herein, one can obtain a suitable membrane from custom membrane fabricators who will use controlled solvent-evaporation and drying methodology[1] (see K. K. Sirkar et al. The effect of short air exposure period on the performance of cellulose acetate membranes from casting solutions with high cellulose acetate content. J. Applied Polymer Sci. 22:1919-1944 (1978) for principles and references) to fabricate a membrane that meets the specification described herein. The narrow end of the pore serves as a bottle-neck to prevent larger molecules like albumin and proteins (MW>50,000) from passing through the pore completely; however, the bottle-neck is the minimum necessary to prevent albumin cross-over and the pore beyond the bottle-neck widens as it courses into the interior of the membrane as shown in FIG. 2b. Therefore, the bottle-neck is said to be dimensioned by the size, geometry and chemistry of the albumin molecule. Since the pore is narrow only at its bottle-neck, in a preferred embodiment the other parts of the pores are large enough to admit albumin molecules. So admitted albumin molecules can come close to the other side of the mebrane, even partially crossing the bottle-neck (FIG. 3). Albumin molecules that come close enough to the other side can contact some adsorbent molecules that reach partially into the pore interior (FIG. 4). In a standard dialysis test cell, albumin-dimensioned bottle-neck pore membrane, of course, tests substantially negative for leakage (cross-over) of larger proteins like serum albumin.

[1] Basically, in the standard membrane casting procedure of Loeb-Sourirajan and Manjikian (references cited by Sirkar article), permeability characteristics of the asymmetric cellulose acetate membrane is governed by the ultra-thin (often under 0.5 microns) skin that one forms on a thicker (typically 8 to 30 microns), large-porous layer. Like the skin that forms on the surface of a hot cup of chocholate milk, the skin of the cellulose acetate membrane forms when a mixture of cellulose acetate with solvents like acetone and formamide is exposed to air. At the air-solvent interphase, the volatile solvent (acetone) evaporates into air leaving a denser concentration of cellulose acetate right at the air-solvent interphase. The pore and thickness characteristic of the skin is governed by how one accomplishes this evaporation. The amount and the rate of evaporation is controllable by such factors as adjusting the environmental temperature (slower evaporation at lower temperature), varying the duration of evaporation, by varying the partial pressure of the evaporating solvent in air, and by using solvents of different volatility (for eample, dioxane has a higher boiling temperature). One can obtain a very thin skin by using a short air exposure time. In this case, one gets a sharply demarcated margin in which very large pores are suddenly adjacent to tiny pores of the skin. To obtain a more gradual transition in the pore dimension, especially within the skin layer, one evaporates slowly over a longer time.

The definition and requirements of albumin-dimensioned bottle-neck pore membrane is functional rather than based on any specific geometry of the pores of the membrane. Different geometric and chemical characteristics at the bottle neck can provide the functional requirements that albumin not be able to completely cross the membrane but that pore dimension elsewhere be large enough so that large molecules like albumin on either side of the membrane are able to come as close as possible to each other, even colliding with each other across the bottle neck to maximize the transfer kinetics of the molecules which are bound to albumin. Other requirements that is fulfilled by this membrane are rather obvious. The membrane is tear resistant for the purpose. Typically, the membrane is about 8 micron thick.

While I believe I am the first to call for the albumin-dimensioned bottle-neck pore membrane, the emphasis in my invention is not to the membrane per se but to the unforeseen new use for this membrane. Since albumin-dimensioned bottle-neck pore membranes can sometimes be no more permeable than standard hemodialysis membrane to unbound solutes, others have failed to see that albumin-dimensioned bottle-neck pore membrane can be so different in removing those solutes when they are bound to albumin in body fluid. When trying to remove molecules that are bound to albumin by using adsorbents across standard hemodialysis membranes, people observed that decreasing the thickness of the membrane even by 66% made no measurable difference. Therefore, it appeared to others the removal of bound molecules did not follow the standard principle that expects better permeability of membrane merely by decreasing its thickness. One commonly finds a statement in journals that a substance is plasma protein-bound and so not dialyzable. I know of otherwise skillful scientists who have wasted many years by not realizing that a different principle applies here and who chose other standard membranes for the task believing no difference existed. I myself stumbled upon the new principle quite by accident when by chance I chose to work with an asymmetric cellulose acetate membrane. While standard asymmetric cellulose acetate membranes used in dialysis are not optimized like the above described albumin-dimensioned bottle-neck pore membrane, I noticed that they worked better than homogeneous hemodialysis membrane like those of regenerated cellulose or polyacrilonitrile in removing molecules that are albumin-bound. I began to explore the reasons and through these reasonings I developed the basis for my invention. I must indeed emphasize that it was entirely unexpected that asymmetric cellulose acetate membranes worked better than polyacrilonitrile membrane because the latter membrane has a better permeability characteristics for free solutes. Yet, I was able to remove zero amounts of bilirubin from serum using polyacrilonitrile membrane with liver cells, while I was able to remove significant amounts of bilirubin using an asymmetric cellulose acetate membrane. Bilirubin, of course, exists in serum almost completely bound to albumin. Both polyacrilonitrile and asymmetric cellulose acetate membrane used in my studies were impermeable to albumin molecules.

During the above membrane comparison studies, I discovered something else that is valuable. In my experiments using asymmetric membranes such as the Celanese Corporation's (Summit, N.J.) CA-1 membrane, I learned that I can remove protein-bound bilirubin from body fluids better if I placed hepatocytes proximate the "active layer" side of the asymmetric membrane. The active layer is commonly known as the skin side of the membrane that governs the porosity. Preferably, the body fluid is made to flow on the underside of the CA-1 membrane with active layer on the top side. Live hepatocytes are placed and layered on top of the membrane. Gravity allows the hepatocytes to sit on the active layer so that they are closely proximate to the active layer.

Figure 5:
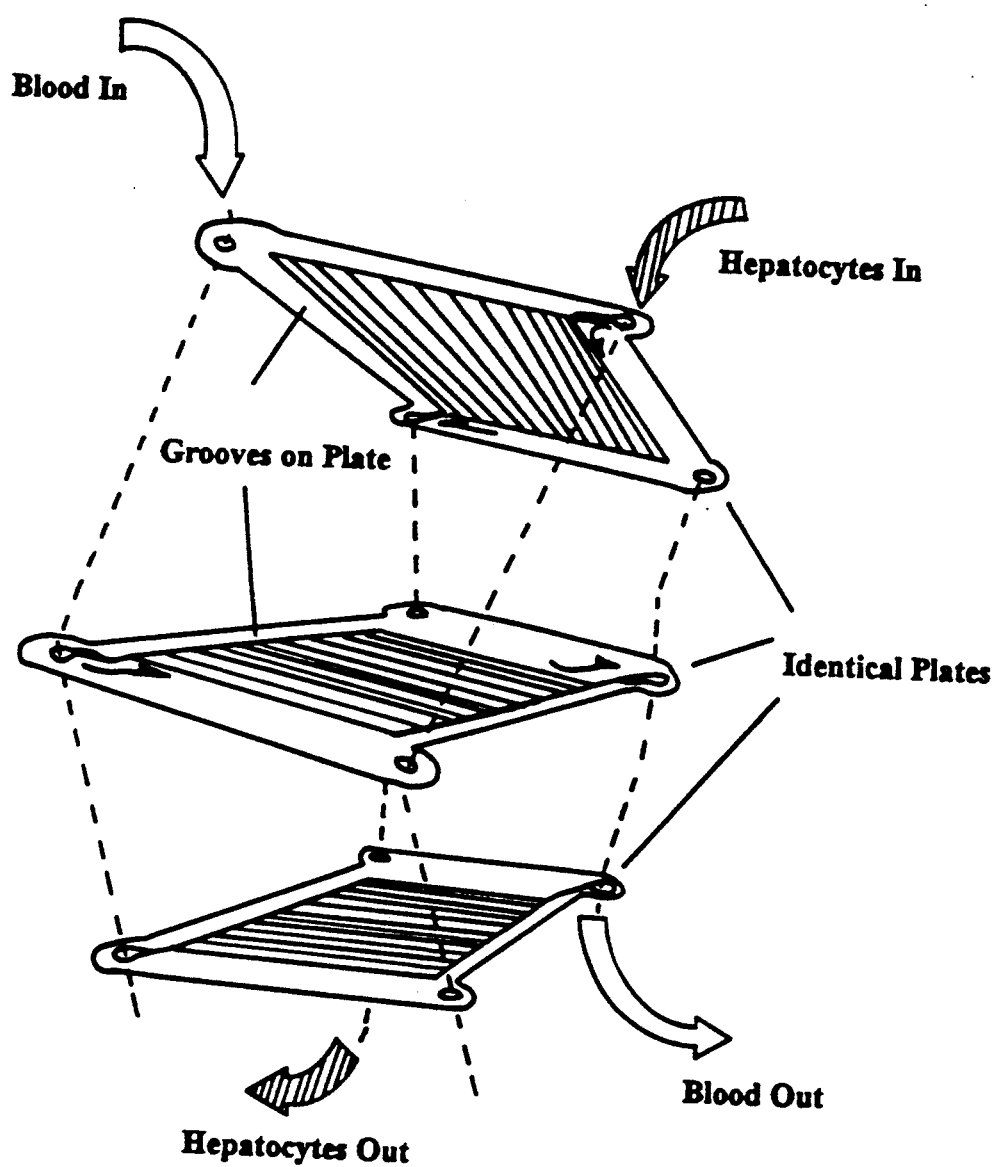
FIG. 5 is a schematic diagram of disposable plastic plates into which grooves are cut to form fluid pathways. Each plate is identical. Because of the pattern of feeding grooves which emanates from corner conduits, all the pathways for blood in different plates are continuous with themselves and all the pathways for fluid suspending hepatocytes are continuous with themselves but not with blood pathways. One treatment module consists of the grooves on the underside of one plate, the grooves on the upperside of the next plate beneath the first, and a semi-permeable membrane sandwiched between the plates. Preferentially, a plurality of many such modules are clamped together between holding plates with multiples bolts around the perimeter of the plates.

Accordingly, I have invented an apparatus (FIG. 5) which consists of multiple stacks of a module which consists of a top multi-groove plate for holding the suspension of hepatocytes or adsorbents and a bottom multi-groove plate for metering the flowing body fluid, said top and bottom plates sandwiching the membrane with the active layer facing the top, cell-adsorbent plate. The direction of the top grooves and the direction of the bottom grooves are perpendicular with respect to one another. Conduit means are provided which connect body fluid pathways of one module with the body fluid pathways of the next module. Likewise, the fluid pathways of the cell-adsorbent chambers of one module is connected to those of the next module. An optimized plates have been adapted by modifying the old, obsolete hemodialyzer Dialung (William Esmond, Fourteen patient-years experience with a simplified hme-hospital chronic hemodialysis system. Trans. Amer. Soc. Artif. Int. Organs 13:254 (1967)) in a manner that meets the specification Just described. (Instead of having the grooves on the upper and under surfaces of a plate being contiguous with each other [via a common cut-through distribution groove and a common cut-through collection groove—see cited article above] and instead of any given plate serving as either the body fluid plate or the dialysis fluid-liver cell plate, the grooves on the underside of a plate serve to hold the liver cells and the grooves on the upper surface, which are made to run perpendicular to the grooves on the underside, serve to meter the flow of the body fluid. The grooves on the upper surface do not connect with the grooves on the underside. The membrane is sandwiched between the grooves on the underside of one plate (holding liver cells) and the grooves on the upper side of another plate beneath the first plate which meter the body fluid. In a preferred embodiment, the grooves of the Dialung type are modified when used for holding hepatocyte suspension by enlarging their volume by forty per cent without changing the distance between grooves. This modification allows for the optimized concentration of flowable (not overly viscous) cell suspension on the semipermeable membrane with respect to the exchange surface area of the membrane and the body fluid flow rate.) Over a period of twelve years, I tested a half a dozen other sandwich type hemodialyzers performing countless number of experiments over hundreds, perhaps thousands, of hours and have discovered unexpectedly that the Dialung configuration is unique and optimal for performing treatment of body fluids with hepatocytes. All the reasons for the uniqueness are not yet known but includes such considerations as dia-filtration properties pertaining to the length of the fluid channels and pressure drop across the fluid pathways. The above module is optimized not only for use with the unique membranes described herein, but also for membranes that allow protein cross-over.

Regarding other components of my invention, by the term adsorbents, I mean such molecules like albumin which bind the molecules to be removed from the body fluid (these are referred to as molecular adsorbents). I also mean tissue homogenates (e.g., liver) which contain a mixture of natural binder molecules like "y" protein in the liver cells which competetively binds bilirubin off of plasma albumin. The adsorbents must be or be made to be, by geometry (size and shape) and chemistry (electrical charge relative to the electrical charge of the wall of the pores), incapable of completely crossing the narrow end of the pores. However, ideally, a substantial portion of the adsorbent molecule could cross the narrow end of the pores and into the depth of the pores (FIG. 4).

By the term adsorbents, I do not limit my definition to a single molecule or a polymer, but I also mean intact cells and cellular fragments or components. Liver cells are functionally active in binding molecules like bilirubin and drugs. The advantage that a cell possesses which a simple molecule does not, is that the cell's binding capacity does not saturate so easily, because typically the cell will also metabolize and/or breakdown molecules it binds so that its binding capacity is renewed in the process. Other cells than liver cells have binding receptors for certain molecules and therefore are useful in removal of such molecules. Unlike simple molecules, cells are also "smart," by which I mean that cells are capable of being more selective in removing harmful molecules over vital ones.

By the term adsorbent, I do not exclude the use of a mixture of adsorbents. In a preferred embodiment of my invention, both a molecular adsorbent, like albumin, and liver cells are used.

Adsorbents must be of size and shape such that they cannot completely cross the membrane. In a preferred embodiment, the adsorbent molecule comprises an extensive binding arm able to cross over the narrow end of the pore and an impedance body incapable of crossing said narrow end. The strength with which adsorbent molecule binds molecules to be removed from body fluids should be comparable to the strength with which albumin binds the molecules to be removed when said adsorbent molecule is to be used together with cell adsorbent. When used alone, such adsorbent molecule may bind molecules more effectively than albumin. Both geometry and chemistry govern the ability of binder arm to cross the narrow end of the pore. Likewise, both geometry and chemistry govern the inability of the impedence body to cross the narrow bottle neck. When such an adsorbent molecule is chemically fabricated, it can be called, "designer adsorbent."

Adsorbent may be commercially purchased. Liver cells can be obtained by the methods of Seglen (Seglen, P. O. Preparation of rat liver cells. *Exp. Cell Res.* 74:450–4 (1974)).

By the term aqueous suspension, I mean that adsorbents are dissolved in or suspended in aqueous fluid, like physiologic salt solution. However, in the case of cells, the term suspension does not mean that the cells are freely floating far away from the surface of the membrane, because the cells need to be proximate the membrane. In the case of the cells, the aqueous fluid merely surrounds the cells, except where the cells are in contact with the membrane.

My invention is preferably practiced with the adsorbent on the narrow pore side (i.e., the active layer side).

In a preferred embodiment, means are provided to cause adsorbents and body fluid proteins on both sides of the membrane to move to-and-fro partially into and out of the membrane pores. The large molecules, of course, do not completely cross the membrane but parts of the molecules may cross the membrane pore's narrow end. For eample, the apparatus of my invention can be placed on a vibrating platform, which allows for rapid to-and-fro movements of suspended molecules. Another example is to cause fluid on either or both sides of the membrane to be made to flow across the surface of the membrane by a peristaltic pump which creates minute, rapid pulsatile flow. While peristaltic pumps are used routinely in hemodialysis application, in this preferred embodiment, I mean to use a modification of such a pump to deliver substantially more pulsations per minute than in standard hemodialysis. This goal can be achieved by adding more rollers to the pump or by decreasing the lumen size of the tubing being squeezed by the rollers and then operating the pump at a higher speed than standard.

In another preferred embodiment, the fluid suspending an adsorbent in contact with the body fluid being treated across the membrane is removed from contact with the membrane, chemically treated to remove bound molecules removed from the body fluid, and returned into contact with the membrane. In this manner, the body fluid is continuously treated by readily binding adsorbents.

In the second part of my invention where the flowing body fluid is treated by hepatocytes more directly across a layer of increased albumin concentration, there are many ways one can make hepatocyte treatment of said body fluid to occur across a thin layer of albumin concentration substantially greater than the concentration in said body fluid. The meaning of what I mean by substantially greater concentration of albumin will become obvious with the examples I will provide on how to achieve the increased concentration of albumin.

Figure 6:
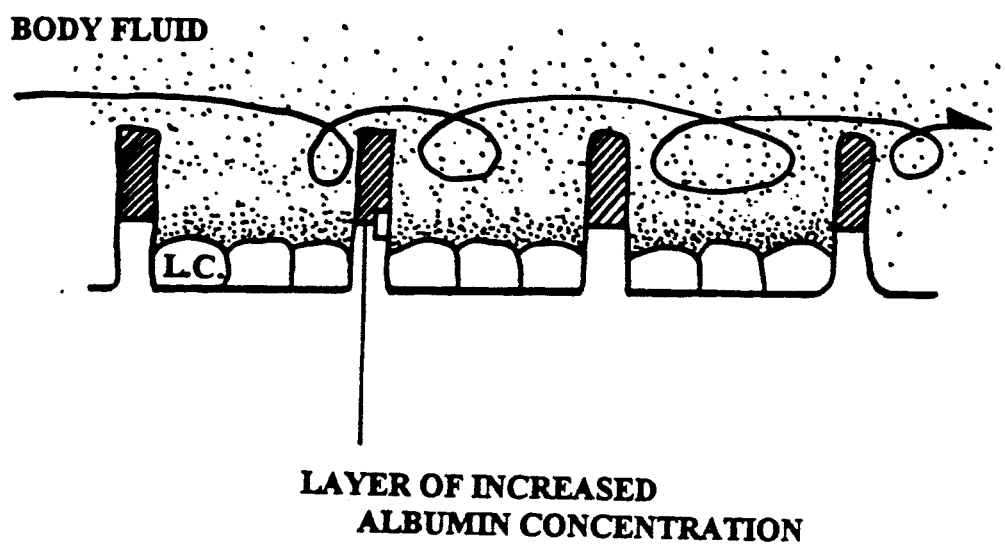
FIG. 6 is a sagittal cross section showing liver cells attached to the bottom of wells or grooves where the cells are not in direct stream of the body fluid. So protected, the liver cells which synthesize albumin and secrete them can form a concentration of albumin on the surface of the liver cells. Cross-hatched areas in the figure indicate surfaces which are made non-attachable to liver cells (e.g., Silastic ® (Dow-Corning Company, Midland, Mich.). Where hepatocytes are seeded onto the inner depth of a groove, body fluid is made to flow perpendicular to the direction of the groove.
Figure 7:
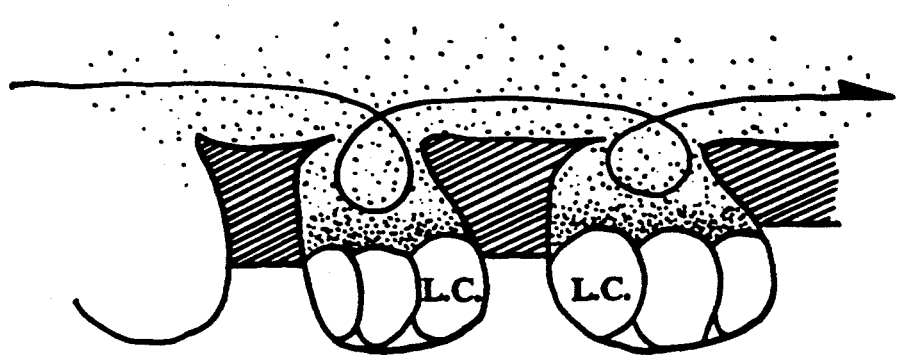
FIG. 7 is a sagittal cross section showing liver cells attached to the bottom of pockets or mini-caverns that can be made to from on many surfaces. As in FIG. 6, the liver cells are not in direct stream of the body fluid and a concentration of albumin can form on the surface of liver cells. As in FIG. 5, cross-hatched areas indicate surfaces which are made non-attachable to liver cells.

One way hepatocyte treatment of flowing body fluid can be made to occur across an increased concentration of albumin is to place the hepatocytes in wells or grooves (FIG. 6) or micro-caverns (FIG. 7). Because the hepatocytes are not in direct stream of the flowing body fluid, albumin synthesized and secreted from hepatocytes will concentrate on the surfaces of the hepatocytes, thereby providing a layer of increased albumin concentration through which the hepatocyte can treat the flowing body fluid at the interphase between the albumin concentrated layer and the body fluid immediately adjacent and distal to the hepatocytes which is rapidly exchanging with the main stream of the flowing body fluid.

It is most important that the body fluid be treated by hepatocytes across a ultrathin layer of increased albumin concentration. In a preferred embodiment, the layer of increased albumin concentration is less than 3 microns.

Figure 8:
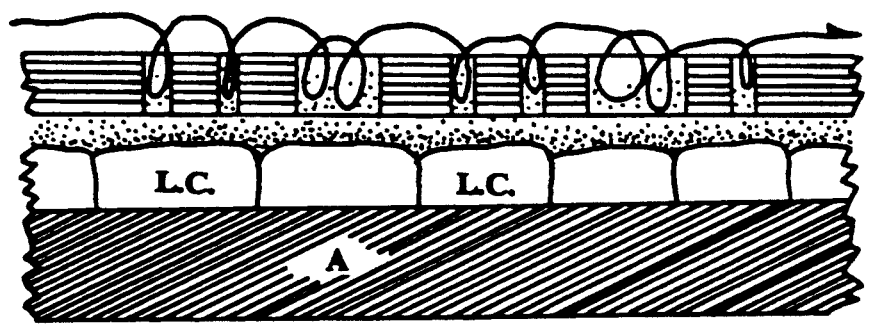
FIG. 8 is a sagittal cross section showing liver cells (L.C.) attached to surface A. A screen-membrane (B) is positioned on the side of the liver cells opposite to surface A. Albumin molecules secreted by liver cells tend to concentrate on the surface of liver cells facing the screen-membrane (B) as well as in the pores of the screen-membrane (B) proximate the liver cells.

In another embodiment (see FIG. 8), a porous screen-membrane is placed over the layer of hepatocytes. The screen-membrane optimally is not one of those "semi-permeable" membranes described in my earlier patent of the bio-artificial liver (previously cited). The purpose of the semi-permeable membrane in my earlier patent was to be truly physiologically semi-permeable, i.e., permeable to molecules but not to immunologic cells. Because of this requirement of "semi-" permeability, the pores of the membrane had to be very narrow, i.e., less than 0.45 microns. The screen-membrane I call for in the instant invention serves an entirely different purpose and is preferably very porous not forming any resistance to cross over of any molecules including albumin. I will explain the reason why a different membrane is preferred.

In the case of the typical commercially available semi-permeable membrane called for in my earlier patent, a layer of increased albumin concentration does form adjacent to the hepatocytes as the hepatocytes synthesize and secrete albumin. This albumin layer extends into the narrow and deep pores of the membrane. However, such a semi-permeable membrane does not enable the formation of a condition I call for in the instant invention, viz., a layer of increased albumin concentration of less than 2 to 3 microns. A typical commercial semi-permeable membranes are between 10 to 30 microns thick and the pores are so narrow that the flowing body fluid does not reach very deeply into the depth of the pores to rapidly exchange the fluid content of the pores. Consequently, the formed albumin layer cannot generally be within 3 microns between the hepatocytes and that portion of the body fluid that is rapidly exchanging with the main stream.

A screen-membrane, on the other hand, can have such large pores as to allow a portion of the body fluid to flow turbulently into the great depth of the pores almost directly touching the hepatocytes on the other side of the membrane. The instant invention performs better the narrower the distance between the hepatocytes and the rapidly exchanging, fluid crest. Screen-membranes with pores of 1 micron in diameter or greater begins to approach something minimally suitable if the screen-membranes is 5 microns in thickness or less. It is preferable that the pores be wider. It is possible to intersperse larger pores of, say, 3 microns among narrower pores, thus allowing greater porosity in a screen-membrane without totally compromising the structural integrity of the membrane. What is important is that the screen-membrane serves as enough of a protective barrier for the hepatocytes to prevent the flowing body fluid from completely washing away the thin layer of increased albumin concentration forming adjacent to the hepatocytes.

Figure 9:
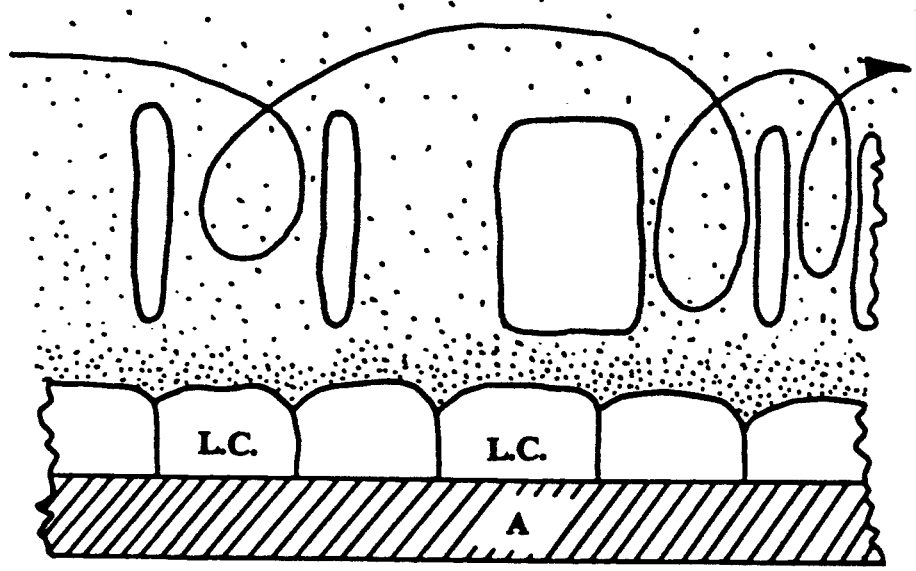
FIG. 9 is a sagittal cross section showing liver cells (L.C.) attached to surface A. A mesh is positioned on the side of the liver cells opposite to surface A. The body fluid flowing across the surface of the mesh is not able to wash away the albumin molecules which are tending to concentrate on the surface of the liver cells because of the thickness of the mesh.

Although the scope of the instant invention could also cover screens, in place of screen-membrane, one finds that it is more challenging to maintain a layer of increased albumin concentration adjacent hepatocytes using a screen because much turbulence is created in the flowing body fluid by the screen. The turbulence tends to wash away any albumin concentration that may be forming at the surface of the hepatocytes, unless the screen has great depth (FIG. 9).

Figure 10:
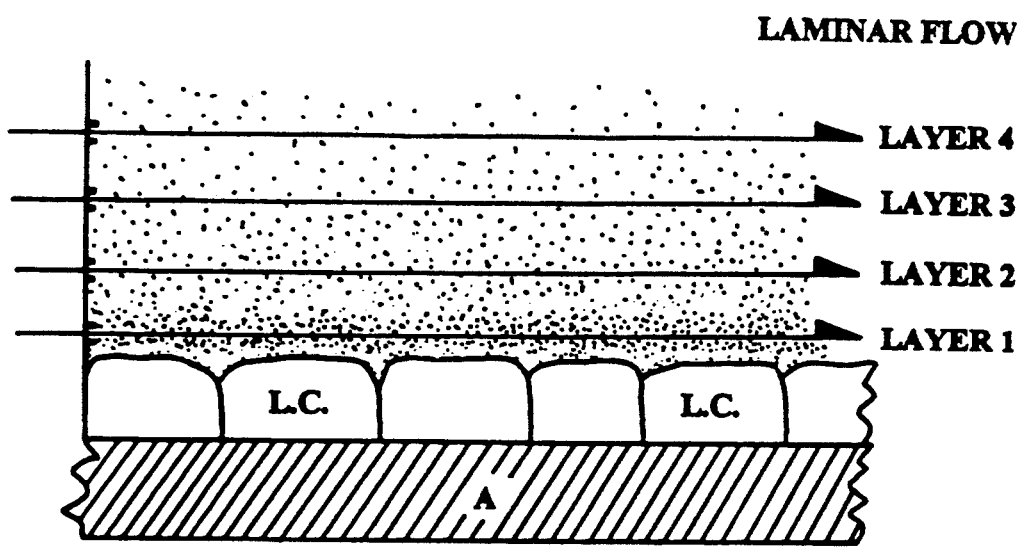
FIG. 10 is a sagittal cross section showing liver cells (L.C.) attached to surface A. The body fluid in a laminar flow passes across the surface of the liver cells. The layer (layer 1) of flowing fluid most proximate to the surface of the liver cells is made to have an increased concentration of albumin.

Yet another way hepatocyte treatment of flowing body fluid can be made to occur across an increased concentration of albumin is to cause a laminar flow of fluid immediately adjacent to the hepatocytes (FIG. 10). This layer of laminar flow fluid will have an increased albumin concentration because the hepatocytes are continually secreting albumin into the layer. (This layer can also be made to have increased albumin concentration by artificially adding albumin into the fluid of this layer.) While the first layer immediately adjacent the hepatocytes and the second layer adjacent the first layer will have to be made to flow at the same rate to maintain the laminar pattern, enhancement of mixing and diffusion can be achieved by flowing the subsequent layers at progressively different rate.

Figure 11:
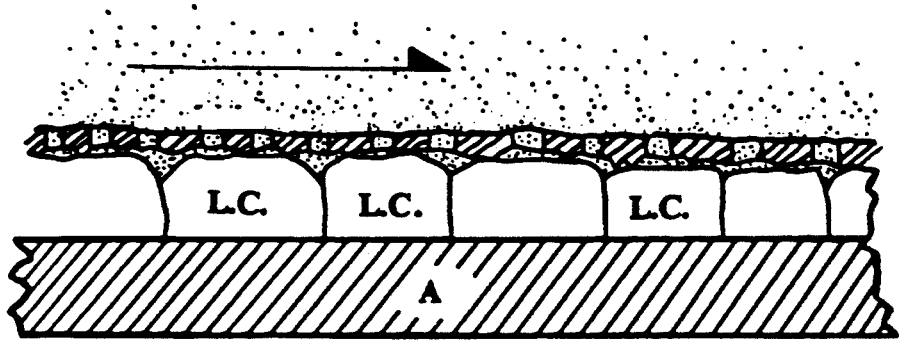
FIG. 11 is a sagittal cross section showing liver cells (L.C.) attached to surface A. Highly porous (porous to albumin) ultra-thin matrix, such as a hydrogel, is formed as a coat on the surface of the liver cells. Albumin tends to concentrate in the pores of the ultra-thin matrix forming a layer of increased concentration of albumin between the liver cells and the flowing body fluid.

In the work of T. Soyer, M. Lempinen, and B. Eiseman (cited above), they suspend liver cells in agar over whose surface body fluid is made to flow (their designated design Mark VII). Although there is discrepancy between the text and the drawing (cited article's FIG. 10), the thickness of the agar-liver layer is described as either 0.5 mm (500 microns) or 4 mm (4000 microns). In their system, a layer of increased albumin concentration may have inadvertently (they had no idea of importance of such a layer) developed between the hepatocytes and the body fluid, but their design would not have worked well. Vast majority of their hepatocytes in agar were not proximate the body fluid, their median distance being either 250 microns or 2000 microns, not the preferred maximum of 3 microns I call for. This is not to say that placing hepatocytes behind a thin 1 to 5 micron thick albumin-porous matrix made of collagen or other material, or imbedding hepatocytes in an albumin-porous matrix barely thick enough to cover them (1 to 5 micron covering), would not be another means of achieving a thin layer of increased albumin concentration between the hepatocytes and body fluid (FIG. 11). Where the porous matrix is as thin as 1 micron, the pore size may be small, even under 0.45 micron, because the two requirements called for in my invention can be met, viz., a thin layer of increased albumin concentration of less than 1-3 microns and close proximity between the hepatocytes and the body fluid that is reaching into the depth of the pores which is rapidly exchanging with the main stream of the body fluid.

My thoughts and requirements are additionally described by the following comments on some interesting work of others.

K. Yanagi et al. (Proc. Am. Soc. Artif. Intern. Organs 35: 570–572, 1989) describe a hybrid artificial liver using hepatocytes entrapped within a hydrogel (calcium alginate). These researchers also cite the work of Y. Miura (Artif. Organs 10(6): 460–465, 1986) and H. Tanaka et al. (Biotechn. & Bioeng. 26:53 –58, 1984) dealing with embedding hepatocytes within hydrogel. Their work actually have little to do with discoveries enumerated in this specification. However, their descriptions reflect the thinking of those who are skilled in the art of designing bioartificial livers. The work of Miura and Tanaka clearly show that albumin cannot diffuse into the hydrogel well. Judging from their description of how the hepatocytes are embedded in hydrogel (between 1.7 to 17 million cells per ml. total volume of hydrogel) as globs of 1.5 mm in diameter (page 461 in Miura cited above) or as a pasted slab on rotating discs, vast majority of the hepatocytes are at a considerable distance from the flowing body fluid and any layer of increased albumin concentration that may develop around the hepatocytes, through which the body fluid must react with the hepatocytes, is on the average too thick. Apparently, albumin secreted by hepatocytes can diffuse out of the gel. Therefore, in the tiny pores of the hydrogel surrounding the hepatocytes, an increased concentration of albumin probably forms. However, their system cannot work efficiently to remove protein (albumin)-bound substances from the body fluid because the average layer of the increased albumin concentration is too thick (hundreds of microns) and the hepatocytes are not proximate to the rapidly exchanging part of the flowing body fluids. As stipulated above, any membrane barrier of my instant invention must not create much resistance to diffusion of molecules such as albumin towards the hepatocytes. According to the teachings of the instant specification, if one were to use a matrix like hydrogel, one can improve the efficiency of the bio-artificial liver by placing the hepatocytes more consistently proximate the rapidly exchanging part of the flowing body fluid and increasing hydrogel permeability for albumin.

It will be obvious to those skilled in the art to find many other ways of making hepatocytes treatment of flowing body fluid to occur across an increased concentration of albumin.

While in this specification, I have referred to flowing body fluid, it is obvious that one can intermittently stop the flow, and the hepatocyte treatment of the body fluid can occur during the time the body fluid is near stationary.

Finally, one can practice the instant invention by first flowing the body fluid to be treated over inexpensive animal hepatocytes across the surface of albumin-dimensioned bottle neck pore membrane then flowing said body fluid over human hepatocytes across a thin layer of increased albumin concentration. The body fluid's toxins can be removed by the combined large mass of animal and human hepatocytes. Vital factors and protein products can be added to the body fluid mainly by the human hepatocytes. The protein products (albumin, clotting factors, etc.) so added will be of human origin and thus not immunogenic to the body fluid being treated. Of course, the instant invention can be practiced in its component parts, separately, as well.

It will be understood that the drawings and specific description have been given for purposes of illustration only and that variations and modifications can be made therein without departing from the spirit and scope of the appended claims.

Having described my invention, I claim:

1. The method of treating body fluid comprising: placing said body fluid proximate the surface of hepatocytes, said hepatocyte treatment of said body fluid being made to occur across a layer of albumin concentration substantially greater than the concentration of albumin in said body fluid, said albumin layer being less than 3 microns.

2. Apparatus comprising: hepatocytes, means for providing and maintaining an increased albumin concentration layer of less than 3 microns adjacent said hepatocytes, and means for positioning body fluid adjacent said layer.

3. Apparatus of claim 2 wherein said means for providing and maintaining an increased albumin concentration layer is an albumin-porous matrix of less than 3 microns.

4. Apparatus of claim 2 wherein said means for providing and maintaining an increased albumin concentration layer is a microcavern provided to attach hepatocytes at inner depth and not at cavern mouth.

5. Apparatus of claim 2 wherein
said means for providing and maintaining an increased albumin concentration layer is a groove provided to attach hepatocytes at inner depth and not at groove opening and
said means for positioning body fluid provide for flow of said body fluid at perpendicular to the direction of said groove.

6. Apparatus comprising plurality of a module comprising an upper plate of multiple, parallel grooves holding a suspension of hepatocytes and a lower plate of multiple, parallel grooves adapted to meter flowing body fluid, said plates sandwiching a semi-permeable membrane, the grooves of said upper plate and the grooves of said lower plate running perpendicular to each other, the grooves of said upper plate being connected to grooves of all upper plates in the plurality of said module, and the grooves of said lower plate being connected to grooves of all lower plates in the plurality of said module.

7. Apparatus of claim 6 wherein the distance between grooves of body fluid plate and hepatocyte fluid plate are identical and the total volume of the hepatocyte fluid grooves of one plate is 40 per cent greater than the total volume of body fluid grooves of the second adjacent plate.

* * * * *